United States Patent
Deshpande et al.

(10) Patent No.: US 11,185,227 B2
(45) Date of Patent: Nov. 30, 2021

(54) METHOD AND SYSTEM FOR AUTOMATED HEALTHCARE MONITORING OF A PATIENT

(71) Applicant: Tata Consultancy Services Limited, Mumbai (IN)

(72) Inventors: Parijat Dilip Deshpande, Kolkata (IN); Arijit Sinharay, Kolkata (IN); Ranjan Dasgupta, Kolkata (IN); Arpan Pal, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 147 days.

(21) Appl. No.: 15/760,709

(22) PCT Filed: Sep. 26, 2016

(86) PCT No.: PCT/IB2016/055737
§ 371 (c)(1),
(2) Date: Mar. 16, 2018

(87) PCT Pub. No.: WO2017/055985
PCT Pub. Date: Apr. 6, 2017

(65) Prior Publication Data
US 2018/0256029 A1    Sep. 13, 2018

(30) Foreign Application Priority Data
Sep. 30, 2015  (IN) .......................... 3720/MUM/2015

(51) Int. Cl.
*A61B 5/00* (2006.01)
*G06F 16/951* (2019.01)
(Continued)

(52) U.S. Cl.
CPC .......... *A61B 5/0022* (2013.01); *A61B 5/6835* (2013.01); *A61B 34/32* (2016.02);
(Continued)

(58) Field of Classification Search
CPC .............................. A61B 34/32; A61B 5/0022
See application file for complete search history.

(56) References Cited

U.S. PATENT DOCUMENTS

2009/0326336 A1    12/2009  Lemke et al.
2012/0130202 A1*    5/2012  Jain ..................... A61B 5/4848
                                                                    600/301
(Continued)

*Primary Examiner* — Rex R Holmes
*Assistant Examiner* — Jennifer L Ghand
(74) *Attorney, Agent, or Firm* — Finnegan, Henderson, Farabow, Garrett & Dunner LLP

(57) ABSTRACT

A system is provided for automated monitoring the health of a patient. The system is unifying the approach of multi-sensing, robotic platform and cloud computing to monitor the health of the patient with zero or very minimal human intervention. The plurality of physiological parameters and the pathological values is sensed using the plurality of physiological sensors and the plurality of pathological sensors or using a smart phone of the patient. The body of the patient is scanned using a robotic arm. The data sensed by the sensor is then identifies a set of anomalies and send the set of anomalies to cloud server. A cognitive engine present on the cloud server is then diagnoses a disease using cloud computing and send the report to caregiver and doctor. According to another embodiment, a method is also provided for automated monitoring the health of the person using the above mentioned system.

11 Claims, 3 Drawing Sheets

(51) Int. Cl.
  G06Q 10/10 (2012.01)
  G16H 40/67 (2018.01)
  G16H 50/20 (2018.01)
  A61B 34/32 (2016.01)
  G16H 70/60 (2018.01)
  G16H 10/60 (2018.01)
  *A61B 5/08* (2006.01)
  *A61B 5/145* (2006.01)
  *A61B 5/318* (2021.01)
  *A61B 5/0205* (2006.01)
  *A61B 5/021* (2006.01)
  *A61B 5/024* (2006.01)

(52) U.S. Cl.
  CPC ........... G06F 16/951 (2019.01); G06Q 10/10 (2013.01); G16H 10/60 (2018.01); G16H 40/67 (2018.01); G16H 50/20 (2018.01); G16H 70/60 (2018.01); *A61B 5/002* (2013.01); *A61B 5/0075* (2013.01); *A61B 5/0077* (2013.01); *A61B 5/021* (2013.01); *A61B 5/0205* (2013.01); *A61B 5/02405* (2013.01); *A61B 5/0816* (2013.01); *A61B 5/14532* (2013.01); *A61B 5/14542* (2013.01); *A61B 5/318* (2021.01); *A61B 5/6898* (2013.01); *A61B 5/7264* (2013.01); *A61B 5/7275* (2013.01)

(56) References Cited

U.S. PATENT DOCUMENTS

| | | |
|---|---|---|
| 2014/0057232 A1 | 2/2014 | Wetmore et al. |
| 2014/0121476 A1* | 5/2014 | Tran .................... A61B 5/0024 600/301 |
| 2014/0170735 A1 | 6/2014 | Holmes |
| 2019/0046037 A1* | 2/2019 | Ramesh ................ G16H 40/67 |
| 2019/0117809 A1* | 4/2019 | Katz ........................ A61L 2/24 |

* cited by examiner

METHOD AND SYSTEM FOR AUTOMATED HEALTHCARE MONITORING OF A PATIENT

CROSS-REFERENCE TO RELATED APPLICATIONS AND PRIORITY

This U.S. patent application claims priority under 35 U.S.C. § 119 to: Indian Application 3720MUM2015 and PCT Application PCT/IB2016/055737, filed on Sep. 30, 2015 and Sep. 26, 2016 respectively.

TECHNICAL FIELD

The present application generally relates to automated healthcare monitoring of a patient. More particularly, but not specifically, the invention provides a system and method for providing automated monitoring and diagnosis aid of a disease of the patient using robotics and cloud computing.

BACKGROUND

There are a lot of medical conditions, when it is very difficult and dangerous for a caregiver or a nurse or a doctor to go near to the patient due to contagious health issues. For example in situations like epidemic outbreaks where it is dangerous for a caregiver to go near to the patient in contagious areas, collect samples, analyze the results and send the diagnosis to doctors for their advice. For example during the time of Ebola attack in 2012, healthcare providers were reluctant to go to the field and help patients because of the possibility of getting infected.

In addition to above scenarios, there are rural places which are remotely located from the civilization. There is scarcity of caregivers in those areas. Further, it is not practically possible for a caregiver to be present at that location all the time. It is desirable to provide home care for such patients. Home care typically requires a periodic visit by a health care provider such as a nurse or some type of assistant. Due to financial and/or staffing issues the health care provider may not be there when the patient needs some type of assistance. Additionally, existing staff must be continuously trained, which can create a burden on training personnel. It would be desirable to provide a system that would allow a health care provider to remotely care for a patient without being physically present.

Various techniques and provisions have been provided to overcome these scenarios. A lot of telemedicine based techniques have been used to cure patients in above two scenarios, but telemedicine based techniques have their own limitation. At least one caregiver or a technician need to be present at both the locations.

The use of robotics have also been explored vastly in the healthcare domain. Using robots in above mentioned cases is becoming more and more popular every day. Robots carrying out surgery, nano-bots delivering drugs inside human body, or therapeutic usage are already in place. Similarly, using Internet of Things (IoT) for telemedicine and tele-pathology or cloud computing for context based data mining are all nothing but a reality today. These demonstrate a tremendous potential of today's technology and if all these technologies are clubbed into a single system, then it can bring us to the next-generation healthcare solution.

One of the robotic system uses an endoscopic camera. The camera allows a surgeon to view a surgical area of a patient and operate the patient from a distant location. But these robots are unable to diagnose the physiological or pathological condition of the patient. Another existing method uses drone for accessing such remote and dangerous locations. The drone robot could fly to the patient, take measurements and inform the hospitals about patient's condition. But these drones are very expensive and very difficult to operate at times.

Various other robotic health care systems have been developed in the past, but none of the system provides a complete end-to-end system which can automatically provide healthcare monitoring of the patient. Therefore, there is a need to provide an end-to-end health care system which can be used by the healthcare providers to monitor the health of the patient from a distant location.

OBJECTIVE

In accordance with the present invention, the primary objective is to provide a system and method for providing an automated healthcare monitoring of a patient using multi-sensing, robotics and cloud computing.

Another objective of the invention is to provide an IoT-enabled robotic system which can be deployed in the field and performed physiological, pathological tests and scanning and send the results to remote healthcare team for further diagnosis.

Yet another objective of the invention is to provide a system and method for providing automated health monitoring of the patient located at a remote location.

Yet another objective of the invention is to provide an end-to-end health care system which can be used by the healthcare providers without being risking their health in case of an epidemic.

Other objects and advantages of the present invention will be more apparent from the following description when read in conjunction with the accompanying figures, which are not intended to limit the scope of the present disclosure.

SUMMARY

Before the present methods, systems, and hardware enablement are described, it is to be understood that this invention is not limited to the particular systems, and methodologies described, as there can be multiple possible embodiments of the present invention which are not expressly illustrated in the present disclosure. It is also to be understood that the terminology used in the description is for the purpose of describing the particular versions or embodiments only, and is not intended to limit the scope of the present invention which will be limited only by the appended claims.

The present application provides a system for automated monitoring the health of a patient, the system comprises a plurality of physiological sensors, a plurality of pathological sensors, a robotic arm, a database, a processor and a cognitive engine. The plurality of physiological sensors senses a plurality of physiological signals of the patient. The plurality of pathological sensors senses and measures a plurality of pathological values of the patient. The robotic arm has a plurality of precision scanners. The plurality of precision scanners scans the body of the patient and generates an output. The database has a data corresponding to a plurality of diseases. The processor comprises an anomaly detection module and a communication module. The anomaly detection module identifies a set of anomalies corresponding to the patient based on the plurality of physiological signals, plurality of pathological values and the output of the precision scanner. The communication module sends the set of anomalies to a cloud server. The cognitive engine is present on the cloud server. The cognitive engine compares the sensors measurements along with the set of anomalies with the data corresponding to the plurality of diseases in the database and generates a report to be sent to a caregiver. The report comprising symptoms of a mapping disease.

According to another embodiment, the invention also provides a method for automated monitoring the health of a patient. Initially a plurality of physiological parameters and a plurality of pathological values are sensed using the plurality of physiological sensors and the plurality of pathological sensors respectively. Also the body of the patient is scanned by the plurality of precision scanners present on the robotic arm. The output is also generated by the precision scanners corresponding to the scanning of the body. A database is also maintained corresponding to the plurality of diseases. In the next step, a set of anomalies are identified corresponding to the patient based on the plurality of physiological signals, the plurality of pathological values and the output of the precision scanner. These set of anomalies are then sent to the cloud server using the communication module. The set of abnormalities are then mapped with the data corresponding to the plurality of diseases to diagnose a disease out of the plurality of diseases. And finally, a report is generated and sent to a caregiver or doctor.

Another embodiment provides a non-transitory computer-readable medium having embodied thereon a computer program for automated monitoring of the health of a patient. The method comprises sensing a plurality of physiological parameters using a plurality of physiological sensors. Further, the method comprises sensing a plurality of pathological parameters using a plurality of pathological sensors, wherein the data comprises physiological and pathological parameters corresponding to the plurality of diseases, wherein the database is a dynamically updatable database depending on a situation. Further, the method comprises scanning the body of the patient using a precision scanner present on a robotic arm and generating an output by the precision scanner corresponding to the scanning of the body. Further, the method comprises maintaining a database of data corresponding to a plurality of diseases, wherein the data comprises physiological and pathological parameters corresponding to the plurality of diseases, wherein the database is a dynamically updatable database depending on a situation. Further, the method comprises identifying a set of anomalies corresponding to the patient based on the plurality of physiological signals, the plurality of pathological values and the output of the precision scanner. Further, the method comprises sending the set of anomalies to a cloud server using a communication module. Further, the method comprises mapping the set of abnormalities with the data corresponding to the plurality of diseases to diagnose a disease out of the plurality of diseases and generate a report. Furthermore, the method comprises sending the report to a caregiver.

BRIEF DESCRIPTION OF THE DRAWINGS

The foregoing summary, as well as the following detailed description of preferred embodiments, are better understood when read in conjunction with the appended drawings. For the purpose of illustrating the invention, there is shown in the drawings exemplary constructions of the invention; however, the invention is not limited to the specific methods and devices disclosed. In the drawings.

DETAILED DESCRIPTION OF THE INVENTION

Figure 1:
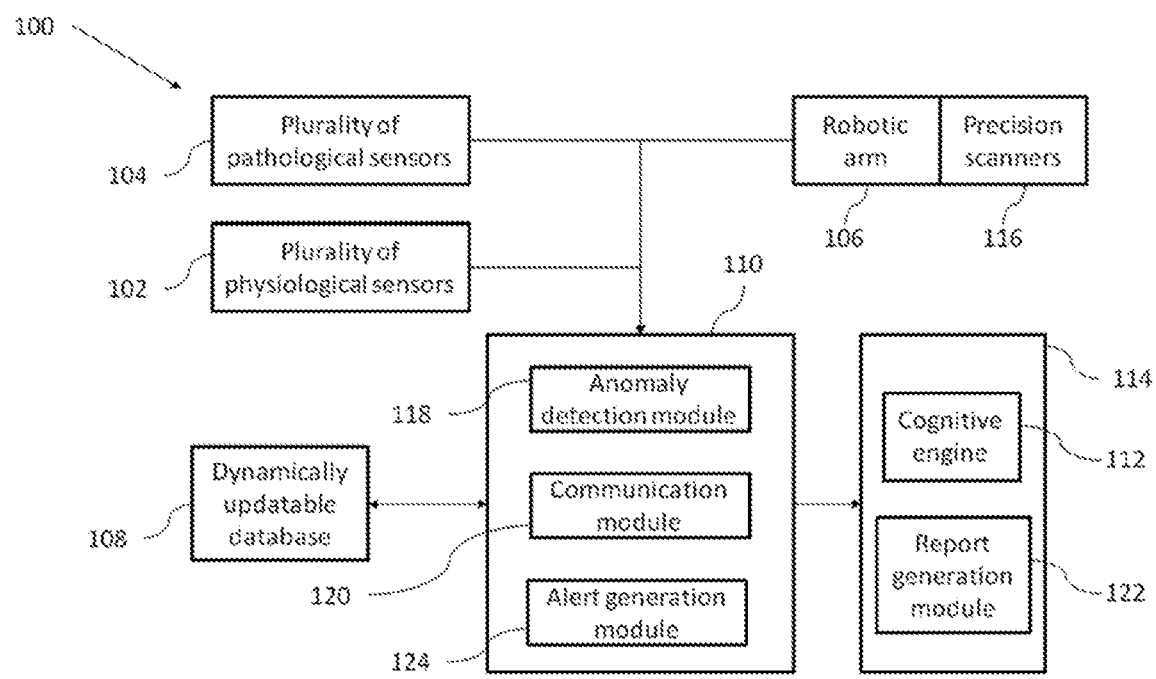
FIG. 1 shows a block diagram illustrating a system for providing automated healthcare to a patient, in accordance with an embodiment of the invention.

Some embodiments of this invention, illustrating all its features, will now be discussed in detail.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software programme executed by any hardware entity for example processor. The implementation of module as a software programme may include a set of logical instructions to be executed by a processor or any other hardware entity.

The disclosed embodiments are merely exemplary of the invention, which may be embodied in various forms.

Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk.

The present application provides a system for automated monitoring the health of a patient, the system comprises a plurality of physiological sensors, a plurality of pathological sensors, a robotic arm, a database, a processor and a cognitive engine. The plurality of physiological sensors senses a plurality of physiological signals of the patient. The plurality of pathological sensors senses and measures a plurality of pathological values of the patient. The robotic arm has a plurality of precision scanners. The plurality of precision scanners scans the body of the patient and generates an output. The database has a data corresponding to a plurality of diseases. The processor comprises an anomaly detection module and a communication module. The anomaly detection module identifies a set of anomalies corresponding to the patient based on the plurality of physiological signals, plurality of pathological values and the output of the precision scanner. The communication module sends the set of anomalies to a cloud server. The cognitive engine is present on the cloud server. The cognitive engine compares the sensors measurements along with the set of anomalies with the data corresponding to the plurality of diseases in the database and generates a report to be sent to a caregiver. The report comprising symptoms of a mapping disease.

According to an embodiment of the present invention, a system 100 for automatic healthcare monitoring of a patient is shown in FIG. 1. The system 100 provides an integrated multi-sensing robotic healthcare system. The system 100 unifies the operation of physiological and pathological sensors, cloud computing and robotics platform to provide automated healthcare monitoring of the patient. The system 100 helps a caregiver or doctor or nurse to diagnose and assess a patient without going close to the patient. In addition to that, the system 100 also configured to diagnose diseases in the patient, generate a corresponding report and sending the report to caregiver or doctor to a remote location.

The system 100 includes a plurality of sensors 102 and 104, a robotic arm 106, a database 108, a processor 110 and a cognitive engine 112 present on a cloud server 114. The system 100 is best suited where there is a scarcity of healthcare providers or deploying them in the field exposes them to high-risk environments. In addition, the system 100 assists routine patient parameter checks and scans in quarantine wards.

The plurality of sensors include a plurality of physiological sensors 102 and a plurality of pathological sensors 104. The plurality of physiological sensors 102 include a blood pressure monitoring device, a photoplethysmograph, a heart rate variability detectors, a temperature sensors and an $SPO_2$ monitor. It should be appreciated that depending on the type of patient or type of disease the use of any other kind of physiological sensors is well within the scope of this invention.

In an embodiment of the invention, the system 100 may also use a smartphone based physiological sensors. In an example, the smartphone based blood pressure (BP), heart rate and heart rate variability (HRV) along with off-the-shelf already available e-health sensor to additionally include breathing rate, ECG, $SPO_2$, temperature and blood glucose measurements. It should be appreciated that the plurality of physiological sensors 102 can also be present on a tablet or independently attached to the patient.

The plurality of pathological sensors 104 include autoanalyzer based sensors. The plurality of pathological sensors 104 can be a microscopy based or a spectroscopy based sensor. The auto-analyzer based measurements can include a large set of pathological tests including detection of virus, bacteria, blood glucose level, cholesterol etc. In an example, the microscope can also be attached to the robotic arm 106 in case of microscopy based sensors.

According to an embodiment of the invention, a robotic platform is provided in the form of the robotic arm 106. It should be appreciated that the use of any other kind of robotic platform is well within the scope of this invention. The robotic arm 106 is configured to move automatically with the help of multiple servo-motors (not shown). The robotic arm 106 is capable of movement as well as fine mechatronics. The robotic arm 106 is further configured to precisely scan the body of the patient. The robotic arm 106 includes a plurality of precision scanners 116 attached therein. The plurality of precision scanners 116 are configured to scan the body of the patient. The plurality of precision scanners 116 further configured to generate a report based on the scanning. The plurality of precision scanners 116 include in-body imaging systems such as Ultrasound imaging, digital stethoscope, ultra wideband (UWB) radar etc. The use of any other kind of imaging techniques is well within the scope of this invention. In another embodiment the thermal and optical camera based sensing can also be used for sensing various other parameters of the patient.

In another embodiment, the robotic arm 106 is also configured to collect the data sensed by the plurality of physiological sensors 102 and the plurality of pathological sensors 104. The data sensed by the plurality of physiological sensors 102, the plurality of pathological sensors 104 and the plurality of precision scanners 116 is sent to the processor 110.

The processor 110 further includes an anomaly detection module 118 and a communication module 120. The anomaly detection module 118 receives the data sensed by the plurality of physiological sensors 102, the plurality of pathological sensors 104 and the plurality of precision scanners 116. The anomaly detection module 118 configured to identify a set of anomalies. The anomaly detection module 118 compares the received data with the standard set of values for a particular physiological or pathological parameters. Based on the comparison, the anomaly detection module 118 identifies a set of anomalies corresponding that particular patient. The set of anomalies are normally define the parameters which are deviating from the normal value. For example, in case of systolic blood pressure measurement, if the measured values move out of the predefined values of 130 to 110 mmHg, then the anomaly detection module 118 will generate an anomaly indicating that the systolic blood pressure of the patient is moving out of the predefined safe limits. It should be appreciated that the set of anomalies generated by the anomaly detection module 118 are with reduced false negative and false positives.

The set of anomalies are then sent to the cloud server 114 using the communication module 120. The communication module 120 can use any of the well-known techniques for communication such as Wi-Fi, Bluetooth, etc. the cloud server 114 generally saves the data on a cloud platform for future use.

According to an embodiment of the invention, the cloud server 114 includes the cognitive engine 112. The cognitive engine 112 is configured to compare the measurements corresponding to the plurality of physiological and pathological sensors 102 and 104 along with the set of anomalies with the data corresponding to the plurality of diseases stored in the database 108. The cognitive engine 112 is connected to this robotic platform via internet for real-time data exchange.

The database 108 includes the data corresponding to a plurality of diseases. In an embodiment the database is also referred as the dynamically updatable database 108. It should be appreciated that the database 108 is configurable and can be customized depending on the situation. The database 108 includes all the standard physiological and pathological parameters corresponding to all the plurality of diseases. For example if patient is suffering from viral fever, then the database 108 will include all the data of hypothetical patient which is required to diagnose the viral fever. According to another embodiment of the invention the cognitive engine 112 can also access an electronic medical record of the patient. The electronic medical record can further help in diagnosing the disease of the patient The cloud server 114 further includes a report generation module 122. The report generation module 122 generates a report and send the report to the caregiver or the doctor. The report comprises the diagnosis of the patient indicating symptoms corresponding to the disease out of the plurality of diseases. The doctor can further analyze the report and send back the prescriptions to the patient.

According to another embodiment of the invention, the system 100 further includes an alert generation module 124. The alert generation module 124 is configured to generate an alert on finding an anomaly or abnormality in the measurements. According to another embodiment of the invention, it should be appreciated that the data in the database 108 can also be adaptively updated based on new findings by the caregivers/doctors.

Figure 2:
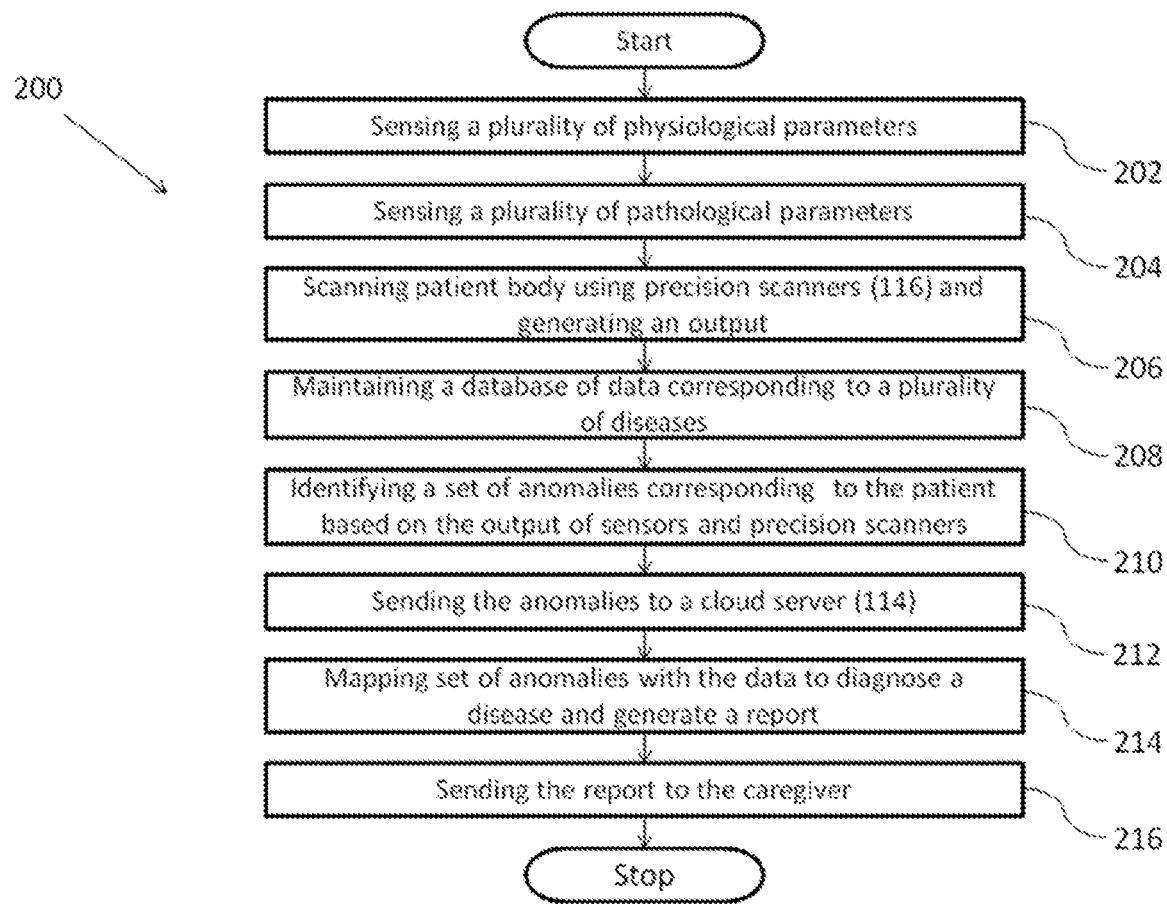
FIG. 2 shows a flow chart illustrating steps involved in automated monitoring the health of a patient in accordance with an embodiment of the invention.

According to an embodiment of the invention, a method for automated monitoring the healthcare of the patient is shown in the flowchart 200 of FIG. 2. Initially at step 202, the plurality of physiological parameters are sensed by the plurality of physiological sensors 102. The plurality of physiological sensors 102 can be smart phone based sensors or attached to the patient body. The plurality of physiological sensors 102 may measure, but not limited to, heart rate, blood pressure, temperature, $SPO_2$, HRV, etc. In the next step at 204, the plurality of pathological values are sensed by the plurality of pathological sensors 104. The plurality of pathological values can be measured using an auto-analyzer based equipment.

In the next step 206, the patient body is scanned by the robotic arm 106. The robotic arm 106 includes the plurality of precision scanners 116. In an embodiment, the robotic arm 106 automatically comes close to the patient and takes measurement using the sensors 102 and 104 and the plurality of precision scanners 116. The use of robotic arm 106 for scanning the body of the patient further increases the efficiency of the plurality of precision scanners 116. The robotic arm 106 also generates an output corresponding to the scanning of the patient body. At next step 208, the database 108 is maintained. The database 108 includes the data corresponding to the plurality of diseases. It should be appreciated that the database 108 is configurable and can be customized depending on the situation. The database 108 includes all the standard physiological and pathological parameters corresponding to all the plurality of diseases. It should also be appreciated that the database can also be updated adaptively over the period of time.

At step 210, a set of anomalies are identified by the anomaly detection module 118. The set of anomalies are identified based on the output of the plurality of precision scanners 116, the plurality of physiological sensors 102 and the plurality of pathological sensors 104. The set of anomalies generally indicates the abnormal condition of the patient pertaining to any parameters. Once the set of anomalies are detected, in next step 212, the set of anomalies are then sent to the cloud server 114 by the communication module 120. In an embodiment, an alert can also be generated by the alert generation module 124, if the set of anomalies move out of predefined range of parameters for a healthy person.

At the next step 214, the set of anomalies are then mapped with the data present in the database. The mapping is done on the cloud server 114 using the cognitive engine 112. The cognitive engine 112 is configured to compare the measurements corresponding to sensors 102, 104 and 116 along with the set of anomalies with the data corresponding to the plurality of diseases in the database 108. Based on the comparison a report is generated by the report generation module 122. And finally at the last step 216, the generated report is then sent to the caregiver/doctor. The doctor can analyze the report to diagnose the disease. In addition to that the doctor can further provide prescriptions and recommendation to cure that disease.

According to another embodiment of the invention, further the LED based reflective photoplethysmograph (PPG) sensor can also be used to extract blood pressure information from wide variety of body positions that supports wearable sensing of the patient. An algorithm is also designed to enable the robotic arm 106 to identify sound source from 3D augmentation obtained from a camera and an array of microphones.

According to another embodiment of the invention, the cognitive engine 112 can also be designed to address smart city public alerting system having novel features like stream windowing, incremental reasoning etc.

An addition to above mentioned advantages of the present system, the doctors can also use this system for their everyday out-patient chambers to take advantage of the number crunching power of machines to eliminate any missed instances in patient's medical records as well as getting inference about the ailment in fraction of a second. Further, various medical data compression techniques with a novel adaptive approach that is best suited for preserving critical information related to abnormalities in the medical data.

Working Example of the Present Invention

According to an embodiment of the present invention, the system 100 can be implemented using smart phone based BP, HR and HRV solutions along with off-the-shelf available eHealth sensor to additionally include breathing rate, ECG, $SPO_2$, temperature and blood glucose measurements. An Arduino board, connected to the smartphone via blue-tooth and connected to eHealth sensors through eHealth shield, is used for sensor data acquisition. The signal from the eHealth sensor is then sent to a processor present in the personal computer via USB connection for alert generation. In the personal computer, the anomaly detection module 118 as well as a cognitive engine 112 both are provided.

Figure 3:
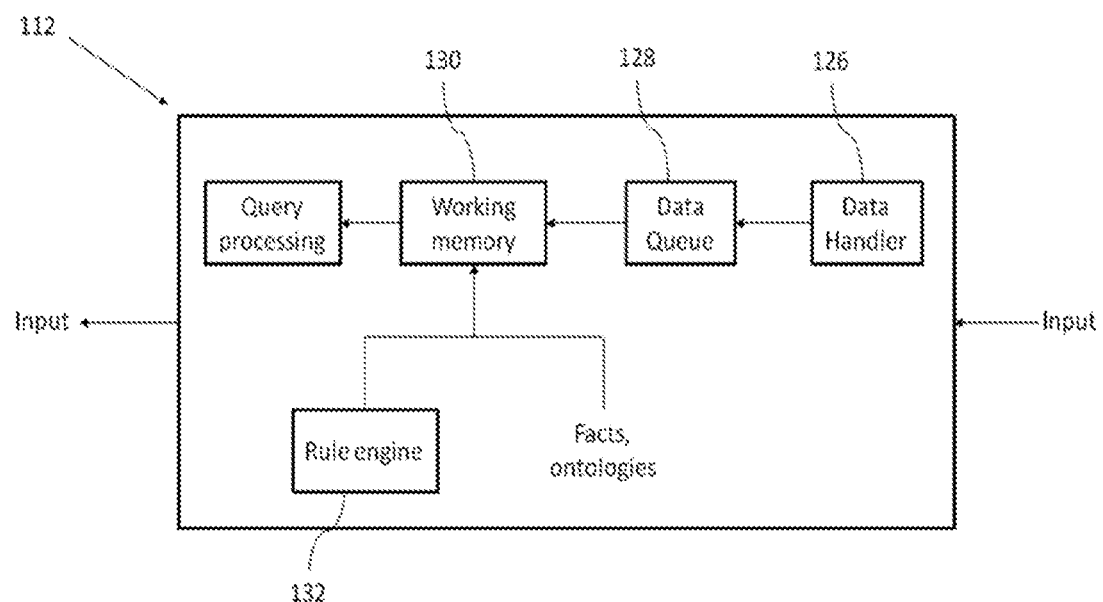
FIG. 3 shows a block diagram illustrating a cognitive engine shown in the embodiment of FIG. 1.

The cognitive engine 112 is based on deriving meaningful actionable inferences by reasoning on the combined knowledge of static facts (like user profile), ontologies (like disease taxonomy) and dynamic facts (like sensed data) as shown in FIG. 3. The input is the sensed data is provided in a queue and processed by a data handler 126. The data handler 126 performs the tasks such as data filtering and transformation) before being put into a data queue device 128 followed by a working memory 130. In the working memory 130, the matching rules are fired and registered queries are triggered at specified intervals to produce results.

The working memory 130 also receives input from a rule engine 132. The present module of cognitive engine 112 is developed by extending Apache Jena7 and is based on Semantic Web framework. The rules are being written in a triple format and so is the query in SPARQL, for knowledge clubbing. Rules are written from medical books and consultation with doctors. A sample rule is to entail stress condition of a patient based on heart rate and blood pressure readings.

(?patient <p:hasHeartRate> <s:high>) (?patient <p:hasBloodPressure> <s:high>)→(?patient <p:possibleDiagnosis> <d:Stress>)

A sample query is: select ?disease where {<u:user123> <p:possibleDiagnosis> ?disease}

Results

It was reported that the successful measurement of BP and HRV parameters when tried on 10 participants. For example, mean error for diastolic (Pd) and systolic pressure (Ps) are under 5% when validated against Omron sphygmomanometer. Similarly, the maximum error in HRV parameters (RMSSD, SDSD, SDNN, nn50, pnn50, nn20, pnn20) are also found to be under 14% when validated against HRV calculated from AliveCor ECG9 data. The rest of the sensing is done with e-Health medical grade sensors and hence, reporting measurement accuracy is not required. The anomaly detection algorithm was executed on the web hosted dataset as all our measurements taken from our colleagues came out to be normal.

In view of the foregoing, it will be appreciated that the present invention provides a system and method for automated monitoring of the health of the patient using multi-sensing, robotic platform and cloud computing. Still, it should be understood that the foregoing relates only to the exemplary embodiments of the present invention, and that numerous changes may be made thereto without departing from the spirit and scope of the invention as defined by the following claims.

We claim:

1. A system for automated healthcare monitoring of a patient, the system comprising:
    a plurality of physiological sensors for sensing a plurality of physiological parameters of the patient;
    a plurality of pathological sensors for sensing and measuring a plurality of pathological parameters of the patient, wherein the measured pathological parameters include an outcome of a set of pathological tests performed on the patient, wherein the plurality of pathological sensors include an auto-analyzer, wherein the auto-analyzer is a microscopy based sensor;
    a robotic arm having a plurality of precision scanners for scanning the body of the patient and generating an output, wherein the microscopy based sensor is attached to the robotic arm, and wherein the robotic arm is configured to collect the sensed plurality of physiological parameters and plurality of pathological parameters and send the sensed plurality of physiological parameters, plurality of pathological parameters and the output of the plurality of precision scanners to a processor;
    a database having data corresponding to a plurality of diseases, wherein the data comprises physiological and pathological parameters corresponding to the plurality of diseases, wherein the database is updated over a regular time interval;
    the processor for,
        receiving, from the robotic arm, the sensed plurality of physiological parameters, plurality of pathological parameters and the output of the plurality of precision scanners;
        identifying a set of anomalies corresponding to the patient based on the sensed plurality of physiological parameters, plurality of pathological parameters and the output of the precision scanners,
        sending the set of anomalies to a cloud server via a wireless connection; and
        generating an alert when the set of anomalies move out of a predefined range; and
    a cognitive engine present on the cloud server, the cognitive engine configured to compare the parameters sensed by the plurality of physiological sensors, the parameters sensed by the plurality of pathological sensors and the set of anomalies, with the parameters corresponding to the plurality of diseases in the database to diagnose a disease out of the plurality of diseases and generating a report to be sent to a caregiver, wherein the report comprising symptoms of the diagnosed disease, and wherein the robotic arm communicates with the cognitive engine via internet in real-time.

2. The system of claim 1 wherein the processor further configured to adaptively update anomaly detection.

3. The system of claim 1 wherein the plurality of physiological sensors are present on at least one of a smart phone, a tablet or independently attached to the patient.

4. The system of claim 3 further comprising an Arduino board connected to the smart phone through a Bluetooth communication for sensors data acquisition.

5. The system of claim 1 wherein the plurality of physiological parameters includes at least one of a blood pressure (BP), heart rate (HR), heart rate variability (HRV) or saturation pressure of oxygen.

6. The system of claim 1 wherein the robotic arm is configured to move in a controlled way with the help of a plurality of servo-motors and mechatronics.

7. A method for automated healthcare monitoring of a patient, the method comprising:
    sensing a plurality of physiological parameters using a plurality of physiological sensors;
    sensing a plurality of pathological parameters using a plurality of pathological sensors, wherein the sensed pathological parameters include an outcome of a set of pathological tests performed on the patient, wherein the plurality of pathological sensors include an auto-analyzer, wherein the auto-analyzer is a microscopy based sensor;
    scanning body of the patient using a plurality of precision scanners present on a robotic arm and generating an output by the plurality of precision scanners corresponding to the scanning of the body, wherein the microscopy based sensor is attached to the robotic arm, and wherein the robotic arm is configured to collect the sensed plurality of physiological parameters and plurality of pathological parameters and send the sensed plurality of physiological parameters, plurality of pathological parameters and the output of the plurality of precision scanners to a processor;
    maintaining a database of data corresponding to a plurality of diseases, wherein the data comprises physiological and pathological parameters corresponding to the plurality of diseases, wherein the database is updated over a regular time interval;

receiving, by the processor, the sensed plurality of physiological parameters, plurality of pathological parameters and the output of the plurality of precision scanners, from the robotic arm;

identifying, by the processor, a set of anomalies corresponding to the patient based on the sensed plurality of physiological parameters, the plurality of pathological parameters and the output of the plurality of precision scanners;

sending the identified set of anomalies to a cloud server via a wireless connection;

generating an alert when the set of anomalies move out of a predefined range;

comparing, by a cognitive engine present on the cloud server, the parameters sensed by the plurality of physiological sensors, the parameters sensed by the plurality of pathological sensors and the set of anomalies, with the data corresponding to the plurality of diseases to diagnose a disease out of the plurality of diseases and generate a report, wherein the report comprises symptoms of the diagnosed disease, and wherein the robotic arm communicates with the cognitive engine via internet in real-time; and sending the report to a caregiver.

8. The method of claim 7 further includes the step of getting an electronic medical record of the patient.

9. The method of claim 7 further includes the step of compressing data corresponding to the set of anomalies identified.

10. The method of claim 7 further includes autonomously approaching the robotic arm towards the patient without the need of human intervention.

11. A non-transitory computer-readable medium having embodied thereon a computer program for automated healthcare monitoring of a patient, the method comprising:

sensing a plurality of physiological parameters of the patient using a plurality of physiological sensors;

sensing and measuring a plurality of pathological parameters of the patient using a plurality of pathological sensors, wherein the measured pathological parameters include an outcome of a set of pathological tests performed on the patient, wherein the plurality of pathological sensors include an auto-analyzer, wherein the auto-analyzer is a microscopy based sensor;

scanning body of the patient using a plurality of precision scanners present on a robotic arm and generating an output, wherein the microscopy based sensor is attached to the robotic arm, and wherein the robotic arm is configured to collect the sensed plurality of physiological parameters and plurality of pathological parameters and send the sensed plurality of physiological parameters, plurality of pathological parameters and the output of the plurality of precision scanners to a processor;

maintaining a database of data corresponding to a plurality of diseases, wherein the data comprises physiological and pathological parameters corresponding to the plurality of diseases, wherein the database is updated over a regular time interval;

receiving, by the processor, the sensed plurality of physiological parameters, plurality of pathological parameters and the output of the plurality of precision scanners, from the robotic arm;

identifying, by the processor, a set of anomalies corresponding to the patient based on the plurality of physiological parameters, the plurality of pathological parameters and the output of the plurality of precision scanners;

sending the identified set of anomalies to a cloud server via a wireless connection;

generating an alert when the set of anomalies move out of a predefined range;

comparing, by a cognitive engine present on the cloud server, the parameters sensed by the plurality of physiological sensors, the parameters sensed by the plurality of pathological sensors and the set of anomalies, with the parameters corresponding to the plurality of diseases to diagnose a disease out of the plurality of diseases and generate a report, wherein the report comprises symptoms of the diagnosed disease, and wherein the robotic arm communicates with the cognitive engine via internet in real-time; and sending the report to a caregiver.

* * * * *